(12) United States Patent
Keimer et al.

(10) Patent No.: US 7,910,060 B2
(45) Date of Patent: Mar. 22, 2011

(54) APPARATUS FOR TREATING PREPARED SPECIMENS

(75) Inventors: Simon Keimer, Nussloch (DE); Harald Rauh, Heidelberg (DE); Eberhard Sendobry, Rimbach (DE); Jürgen Tenhaef, Brombachtal (DE); Stefan Thiem, Heidelberg (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 72 days.

(21) Appl. No.: 12/559,112

(22) Filed: Sep. 14, 2009

(65) Prior Publication Data

US 2010/0068094 A1  Mar. 18, 2010

(30) Foreign Application Priority Data

Sep. 16, 2008 (DE) .......................... 10 2008 047 414

(51) Int. Cl.
*G01N 21/00* (2006.01)
(52) U.S. Cl. ............... 422/63; 422/64; 422/65; 422/99; 422/100; 436/180
(58) Field of Classification Search ............. 422/63–65, 422/99–100; 436/180
See application file for complete search history.

(56) References Cited

FOREIGN PATENT DOCUMENTS

| DE | 10041231 | 3/2002 |
|---|---|---|
| DE | 10149345 | 5/2003 |
| EP | 0490084 | 6/1992 |
| EP | 0849582 | 6/1998 |
| EP | 0884577 | 12/1998 |
| GB | 2359130 | 8/2001 |

*Primary Examiner* — Jyoti Nagpaul
(74) *Attorney, Agent, or Firm* — Schlee IP International, P.C.; Alexander R. Schlee

(57) ABSTRACT

An apparatus is described for treating prepared specimens. The apparatus comprises at least two container rows arranged in parallel to each other, each comprising a plurality of reagent containers and a transport mechanism for transporting at least one transport container that receives at least one carrier holding at least one prepared specimen. The transport mechanism is movable along an X and Z axis. A rotation unit is provided comprising holding arms and at least one holding element. The container rows are received rotatably at the ends of the holding arms of the at least one holding element that is connected to a rotation shaft such that it co-rotates with the rotation shaft that extends parallel to the X axis. The rotation unit is adapted to assume at least one working position allowing the transport mechanism to have access to the reagent container.

13 Claims, 3 Drawing Sheets

APPARATUS FOR TREATING PREPARED SPECIMENS

CROSS-REFERENCE TO RELATED APPLICATION

This application claims the priority of the German patent application DE 102008047414.2 having a filing date of Sep. 16, 2008. The entire content of this prior German patent application DE 102008047414.2 is herewith incorporated by reference.

BACKGROUND OF THE INVENTION

The invention refers to an apparatus for treating prepared specimens that comprises at least two container rows arranged in parallel fashion, each container row having a plurality of reagent containers that are filled with different reagents. The apparatus further comprises a transport mechanism for transporting at least one transport container. The transport container receives at least one carrier on which at least one prepared specimen is mounted. The transport mechanism is movable at least in the direction of an X axis along the longitudinal axis of the container rows, and in a Z axis arranged transversely to the X axis.

An apparatus of this kind for treating prepared specimens is known, for example, from the document GB 2 359 130 A. In this apparatus, two container rows are arranged in parallel fashion directly next to one another, producing a matrix-like structure. Individual carriers, or transport baskets having multiple carriers, are immersed into the containers filled with reagents, or removed from the containers, by way of a slider-like transport mechanism. The apparatus further comprises a heating unit to heat the prepared specimens or to melt the medium in which the prepared specimens are embedded.

A further apparatus for treating prepared specimens is known from the document EP 0 884 577 B1. The apparatus takes the form of a cabinet. The apparatus comprises a lower and an upper plate on each of which are arranged multiple reagent containers. The apparatus further comprises a transport mechanism with which transport baskets, in which carriers having the prepared specimens are located, can be transported between the individual reagent containers. The upper plate further comprises a passthrough through which the transport baskets can be transported from the upper plate to the lower plate.

A further apparatus for treating prepared specimens is known from the document EP 0 849 582 B1. The apparatus comprises multiple reagent containers that are arranged in a matrix-like structure in one tier. The apparatus furthermore comprises a transport mechanism that transports the carriers having the prepared specimens, or transport baskets having the carriers, between the reagent containers.

A disadvantage of the known apparatuses for treating prepared specimens is the low throughput of prepared specimens resulting from the configuration of the apparatuses for treating prepared specimens. As a rule, multiple transport containers are treated simultaneously in the apparatus. Because the known apparatuses each comprise only one transport mechanism, the transport time duration of the transport containers is the factor that limits the throughput of prepared specimens. Because the speed at which the transport containers are transported cannot be arbitrarily increased, the prepared-specimen throughput of the apparatuses is limited. As a result of the matrix-like arrangement of the transport containers in one or more tiers, the transport distances that must be traversed by a transport container during transport from one reagent container to another is relatively large, and the transport time duration is long. The use of multiple transport mechanisms in one apparatus is problematic because overlaps occur between the working regions of the individual transport mechanisms, thereby creating a risk of collisions of the transport containers or carriers. This can result in damage to the carriers and/or to the prepared specimens. A complex control mechanism of correspondingly high calculation complexity is necessary in order to avoid such collisions.

A further problem with apparatuses for treating prepared specimens is the contamination of reagents in one reagent container by other reagents. In general, as a transport container or carrier is transported from one reagent container to a subsequent reagent container, other reagent containers are traveled over. Reagents of the reagent container in which the transport container was most recently located usually still adhere to the transport container or carrier. Gravity causes the formation of droplets that, as the transport container or carrier travels over the reagent containers, drip off and into the reagent containers being traveled over, thus contaminating the reagents present in the reagent containers being traveled over.

The apparatus for treating prepared specimens that is known from the document EP 0 849 582 B1 therefore comprises a unit that, during transport of a transport container, is pivoted beneath the transport container in order thereby to prevent the contamination of reagent containers that are traveled over during transport. An absorbent material is advantageously applied onto this unit in order to prevent reagents from dripping off the unit. The disadvantages of this apparatus are on the one hand that an additional mechanism is necessary, and on the other hand that a corresponding control complexity is created. It is furthermore disadvantageous that the absorbent material must be regularly replaced.

SUMMARY OF THE INVENTION

It is an object of the invention to describe an apparatus for treating prepared specimens that guarantees a high prepared-specimen throughput and is of simple configuration.

This object is achieved by an apparatus for treating prepared specimens, comprising: at least two container rows arranged in parallel to each other, each comprising a plurality of reagent containers; a transport mechanism for transporting at least one transport container that receives at least one carrier holding at least one prepared specimen, the transport mechanism being movable at least in a first direction along an X axis extending along a longitudinal axis of the reagent containers, and in a second direction along a Z axis extending transversely to the X axis; and a rotation unit comprising holding arms and at least one holding element; wherein the container rows are received rotatably at the ends of the holding arms of the at least one holding element that is connected to a rotation shaft such that it co-rotates with the rotation shaft that extends parallel to the X axis; and wherein the rotation unit is adapted to assume at least one working position allowing the transport mechanism to have access to the reagent container.

According to the invention, the apparatus comprises a rotation unit that receives the container rows, which are mounted rotatably at the ends of holding arms of at least one holding element of the rotation unit, which element is joined nonrotatably to a rotation shaft extending parallel to the X axis. In addition, at least one working position of the rotation unit is defined in which the transport mechanism has access to the reagent container. Mounting of the reagent containers in the rotation unit enables movement of the reagent containers. In addition to the movement of the transport containers by way of the transport mechanism, a second movement is thereby additionally implemented. The result of this is on the one hand that the transport distance that a transport container must traverse while it is being transported from one reagent container to the next transport container is shorter, so that in turn the transport time duration is reduced and the throughput of prepared specimens is increased. In addition, arranging the reagent containers in the rotation unit makes it possible for transport of the transport containers from one reagent container to another reagent container to take place without traveling over a further reagent container. Contamination of the reagents of a reagent container by reagents that drip off during transport from the transport containers, or from the carriers that are present in the transport container, is accordingly precluded.

In an advantageous refinement of the invention, the rotation unit comprises multiple cross-shaped holding elements that are joined nonrotatably to the rotation shaft, the rotation shaft extending through the center points of the holding elements. As a result of the cross shape of the holding elements, and the symmetrical arrangement of the container rows resulting therefrom, the control complexity of the rotation unit is reduced.

It is additionally advantageous that the transport mechanism comprises a further axis that is orthogonal to the X axis and orthogonal to the Z axis. As a result of this further degree of movement of the transport mechanism, the transport baskets can also be delivered to or removed from reagent containers that are arranged outside the rotation unit.

Transport baskets, in particular, are used as transport containers. The basket-like shape of the transport containers on the one hand enables good wetting of the carriers present on the transport container, and of the prepared specimens mounted on the carriers. On the other hand, the basket shape enables the reagents to drip off effectively even before the transport basket has completely left the reagent container.

It is further advantageous that the apparatus comprises at least one stationary container row that is arranged outside the rotation unit and comprises a plurality of reagent containers. Arranged in this stationary container row are, in particular, reagent containers that cannot be arranged in the rotation unit. These are, in particular, reagent containers with running water that serve to rinse the prepared specimens.

It is additionally advantageous that one reagent container is rotatably mounted between each two adjacent elements of the rotation unit, at the ends of the holding elements. The result is that the reagent containers can be individually removed from or delivered to the rotation unit.

In an advantageous refinement of the apparatus for treating prepared specimens, a small drip pan is arranged beneath the stationary container row. This drip pan receives the reagents dripping off from the transport container or the carriers during transport, thus avoiding soiling of the apparatus or of other objects present in the vicinity of the apparatus.

It is additionally advantageous that a second drip pan is arranged beneath the rotation unit and the small drip pan, offering a further capability for intercepting reagents dripping off from the transport container or the carriers.

It is furthermore advantageous that in the working position, the rotation unit is rotated in such a way that at least one holding arm of each holding element is horizontal, and the reagent container of the rotation unit that is being accessed by the transport mechanism is arranged on at least one of the horizontal holding arms and is arranged in that container row which faces toward the stationary container row. The transport distance that the transport container must traverse from one reagent container to the next reagent container is thereby minimized, so that in turn the transport time duration is reduced and the throughput of prepared specimens is thereby increased.

BRIEF DESCRIPTION OF THE DRAWINGS

Further features and advantages of the invention are apparent from the description that follows, which explains the invention with reference to an exemplifying embodiment in combination with the attached Figures, in which.

DETAILED DESCRIPTION OF THE DRAWINGS

Figure 1:
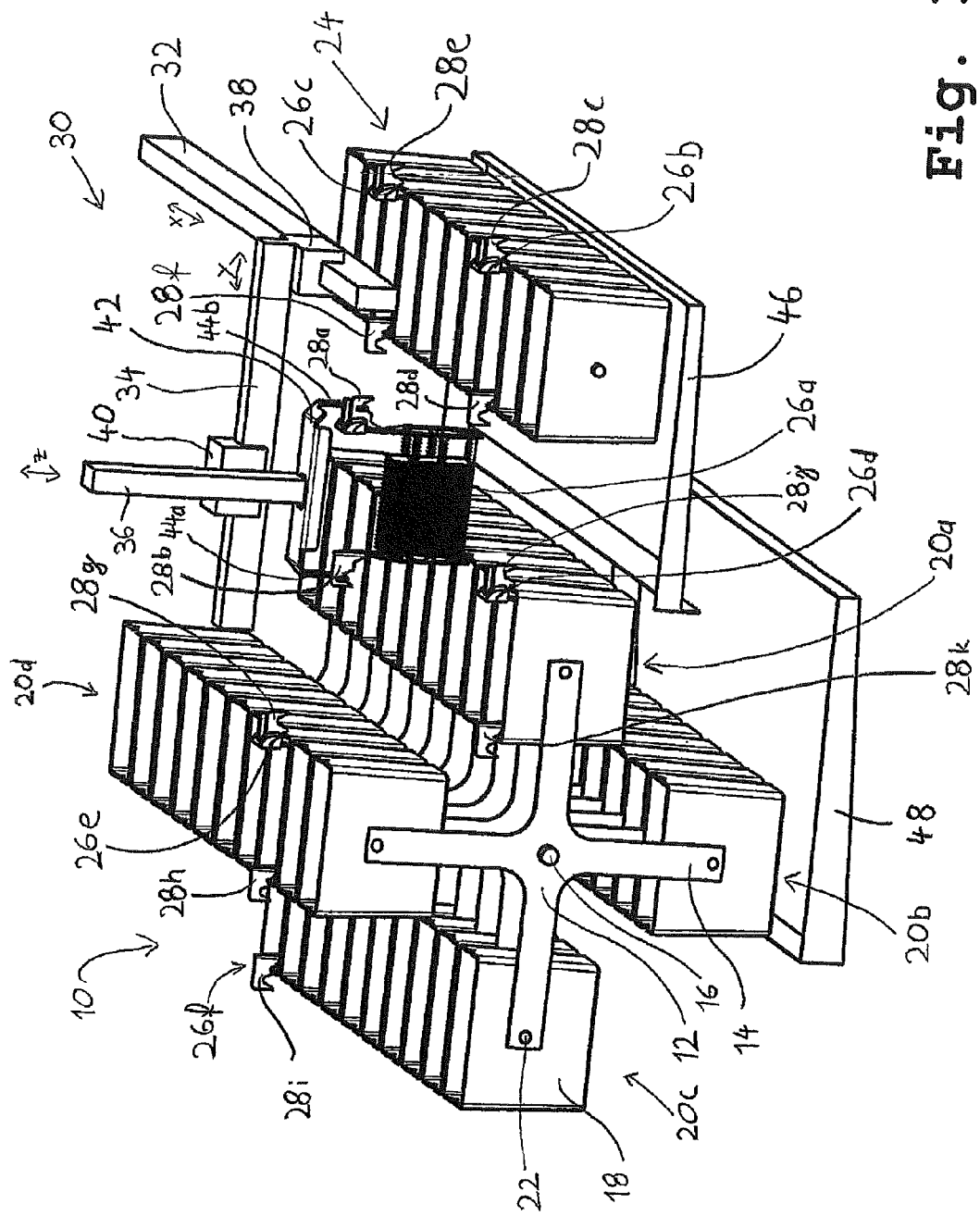
FIG. 1 is a perspective depiction of an apparatus for treating prepared specimens, in a working position.

FIG. 1 shows an apparatus for treating prepared specimens, in a working position. The apparatus has a rotation unit 10 that in turn comprises a plurality of holding elements 12. Each holding element 12 comprises four holding arms 14 that are arranged in a cross shape. Holding element 12 is therefore also referred to as a holding cross 12. Holding crosses 12 are arranged in such a way that their center points lie on a common rotation shaft 16. Holding crosses 12 are joined nonrotatably to rotation shaft 16. Each two adjacent holding crosses 12 are at the same distance from one another.

On holding arms 14 of holding crosses 12, one reagent container is arranged between each two adjacent holding crosses 12. One of these reagent containers is labeled, by way of example, with the reference number 18. Reagent containers 18 are also referred to as "cuvettes." These reagent containers 18 are each joined rotatably via an axle element 22 to holding arms 14 of holding crosses 12. Reagent containers 18 can thus be individually removed from rotation unit 10 and individually delivered to rotation unit 10. All the reagent containers 18 that are attached to holding arms 14 of holding crosses 12 directed in the same direction are also referred to together as a container row 20a to 20d. Rotation unit 10 thus comprises four container rows 20a to 20d.

Reagent containers 18 are filled with reagents that serve, for example, to stain prepared specimens. Such reagents can be, for example, solvents, dye solutions, or water.

The apparatus for treating prepared specimens further comprises one stationary container row 24. This stationary container row 24, unlike the other container rows 20a to 20d, is arranged outside rotation unit 10 and is thus immovable. Stationary container row 24 comprises a plurality of reagent containers 18. Arranged in stationary container row 24 are, in particular, reagent containers 18 that are not suitable for placement in rotation unit 10. These are, for example, reagent containers 18 that are impinged upon by running water.

Multiple transport containers 26a to 26f are placed into reagent containers 18. Transport containers 26a to 26f are advantageously transport baskets 26a to 26f, which are also often referred to as "racks." Each transport basket comprises at its upper end two respective hooks 28a to 28k whose spacing from one another is exactly the same as the length of one reagent container 18. When a transport basket 26a to 26f is placed into a reagent container 18, the two hooks 28a to 28k then rest on the two oppositely located short edges of the container opening of reagent container 18.

Transport baskets 26a to 26f can each receive at least one carrier. The carriers are, in particular, glass carriers that are also referred to as "slides." These carriers are concealed by transport baskets 26a to 26f in FIG. 1 and are thus not depicted. At least one prepared specimen is mounted onto each such carrier. These prepared specimens are, in particular, thin sections of biological material.

Treatment of the prepared specimens, in particular staining of biological material, is accomplished by placing one of transport baskets 26a to 26f into a reagent container 18, leaving it there for a predefined time, then removing it from reagent container 18, transporting it to a further reagent container 18, and placing it thereinto. This operation can occur several times during the treatment of a prepared specimen.

Transport baskets 26a to 26f are transported from one reagent container 18 to another reagent container 18 with the aid of a transport mechanism 30. In the exemplifying embodiment depicted, transport mechanism 30 is a linear transport mechanism having three linear axes 32 to 36. Other transport mechanisms are, however, also possible.

The three linear axes 32 to 36 of transport mechanism 30 are arranged orthogonally to one another. First linear axis 32 is arranged in the direction of an X axis along the longitudinal axis of container rows 20a to 20d, 24. Second linear axis 34 is arranged orthogonally to first linear axis 32 and extends horizontally. Second linear axis 34 is joined fixedly to a first slider 38. First slider 38 is displaceable on first linear axis 32 in the direction of the X axis. Second linear axis 34 is directed in the direction of a Y axis.

Transport mechanism 30 further comprises a third linear axis 36 that is arranged orthogonally to first linear axis 32 and orthogonally to second linear axis 34. The longitudinal axis of third linear axis 36 proceeds in the direction of the Z axis. Third linear axis 36 is joined, movably in the direction of the Z axis, to a second slider 40. Second slider 40 is arranged, displaceably in the direction of the Y axis, on second linear axis 34.

Arranged at the end of third linear axis 36 facing toward rotation unit 10 is a gripper 42 that is joined fixedly to third linear axis 36. Gripper 42 has two hooks 44a, 44b. The spacing from one another of hooks 44a, 44b of gripper 42 is exactly the same as the spacing from one another of hooks 28a to 28k of transport baskets 26a to 26f. When a transport basket 26a to 26f is to be transported, gripper 42 is moved with the aid of transport mechanism 30 in such a way that hooks 44a, 44b of gripper 42 are located beneath hooks 28a to 28k of transport basket 26a to 26f to be transported. Gripper 42 is then lifted with the aid of transport mechanism 30, hooks 44a, 44b of gripper 42 engaging into hooks 28a to 28k of transport basket 26a to 26f that is transported.

Rotation unit 10 is shown in FIG. 1 in the working position, in which transport mechanism 30 has access to reagent containers 18. This working position is characterized in that in the working position, rotation unit 10 is rotated in such a way that at least one holding arm 14 of each holding cross 12 is horizontal, and that reagent container 18 of rotation unit 10 to which transport mechanism 30 has access is arranged on at least one of horizontal holding arms 14 and is arranged in that container row 20a which faces toward stationary container row 24. Transport basket 26a to 26f to be transported is transported in such a way that gripper 42 is moved with the aid of transport mechanism 30 in such a way that hooks 44a, 44b of gripper 42 are located beneath hooks 28a to 28k of transport basket 26a to 26f to be transported. Gripper 42 is then lifted with the aid of transport mechanism 30, in the direction of the Z axis, until the lower end of transport basket 26a to 26f to be transported is located above the opening of reagent container 18 from which transport basket 26a to 26f is to be removed. Transport basket 26a to 26f is then moved, with the aid of transport mechanism 30, in the Y-axis direction until transport basket 26a to 26f to be transported is no longer located above reagent container 18 from which transport basket 26a to 26f was to be removed. Transport basket 26a to 26f to be transported is, however, moved in the Y-axis direction only sufficiently far that it is not yet located above stationary container row 24. The distance between the container row 20a of rotation unit 10 from which transport basket 26a to 26f to be transported is removed, and stationary container row 24, is greater than the width of transport basket 26a to 26f.

If transport basket 26a to 26f to be transported is to be transported into a reagent container 18 of stationary container row 24, then in the next step, transport basket 26a to 26f is transported in the X direction until it is located next to reagent container 18 into which it is to be transported. Transport basket 26a to 26f to be transported is then moved, with the aid of transport mechanism 30, in the Y-axis direction until transport basket 26a to 26f to be transported is located above the reagent container 18 of stationary container row 24 into which it is to be placed. In the next step, transport container 26a to 26f to be transported is lowered in the Z-axis direction until it is located in that reagent container 18 of stationary container row 24 into which it was to be transported.

If transport basket 26a to 26f to be transported is to be transported not into a reagent container 18 of stationary container row 24, but into another reagent container 18 of rotation unit 10, rotation unit 10 is then rotated until reagent container 18 into which transport basket 26a to 26f to be transported is to be transported is located in the container row 20a that faces toward stationary container row 24. Simultaneously with this rotation, transport basket 26a to 26f to be transported is transported, with the aid of transport mechanism 30, in the X-axis direction until it is located next to that reagent container 18 of rotation unit 10 into which it is to be transported. In the next step, transport basket 26a to 26f to be transported is moved, with the aid of transport mechanism 30, in the Y-axis direction until it is located above reagent container 18 into which it is to be placed. Transport basket 26a to 26f to be transported is then lowered, with the aid of transport mechanism 30, in the Z-axis direction until transport basket 26a to 26f to be transported is located in reagent container 18 into which it is to be transported.

Delivery of a transport basket 26a to 26f to be transported to the apparatus for treating prepared specimens, and removal of a transport basket 26a to 26f to be transported from the apparatus for treating prepared specimens, are accomplished by a user by the fact that the user places transport basket 26a to 26f into a reagent container 18 of stationary container row 24 or removes it from a reagent container 18 of stationary container row 24.

The apparatus for treating prepared specimens further comprises a small drip pan 46 and a large drip pan 48. Small drip pan 46 is located below stationary container row 24. The large drip pan is arranged below the small drip pan and below rotation unit 10. Small drip pan 46 serves to collect reagent drops that drip, during the transport of transport basket 26a to 26f in the X-axis direction, from transport basket 26a to 26f and/or from the carrier or carriers that are in transport basket 26a to 26f. The transport of transport baskets 26a to 26f in the X-axis direction occurs exclusively above small drip pan 26. As they are transported by transport mechanism 30, transport baskets 26a to 26f are not transported above reagent containers 18, except for reagent container 18 from which transport basket 26a to 26f is removed, and reagent container 18 into which transport basket 26a to 26f is placed. This prevents contamination of the reagents of a reagent container 18 by drops of reagents that drip, during the transport of transport basket 26a to 26f, from transport basket 26a to 26f and/or from the carriers present in transport basket 26a to 26f.

Large drip pan 48 is arranged in such a way that the reagents that drip into small drip pan 46 run from small drip pan 46 into large drip pan 48. Both small drip pan 46 and large drip pan 48 prevent the soiling of other apparatuses that are located below the apparatus for treating prepared specimens.

Figure 2:
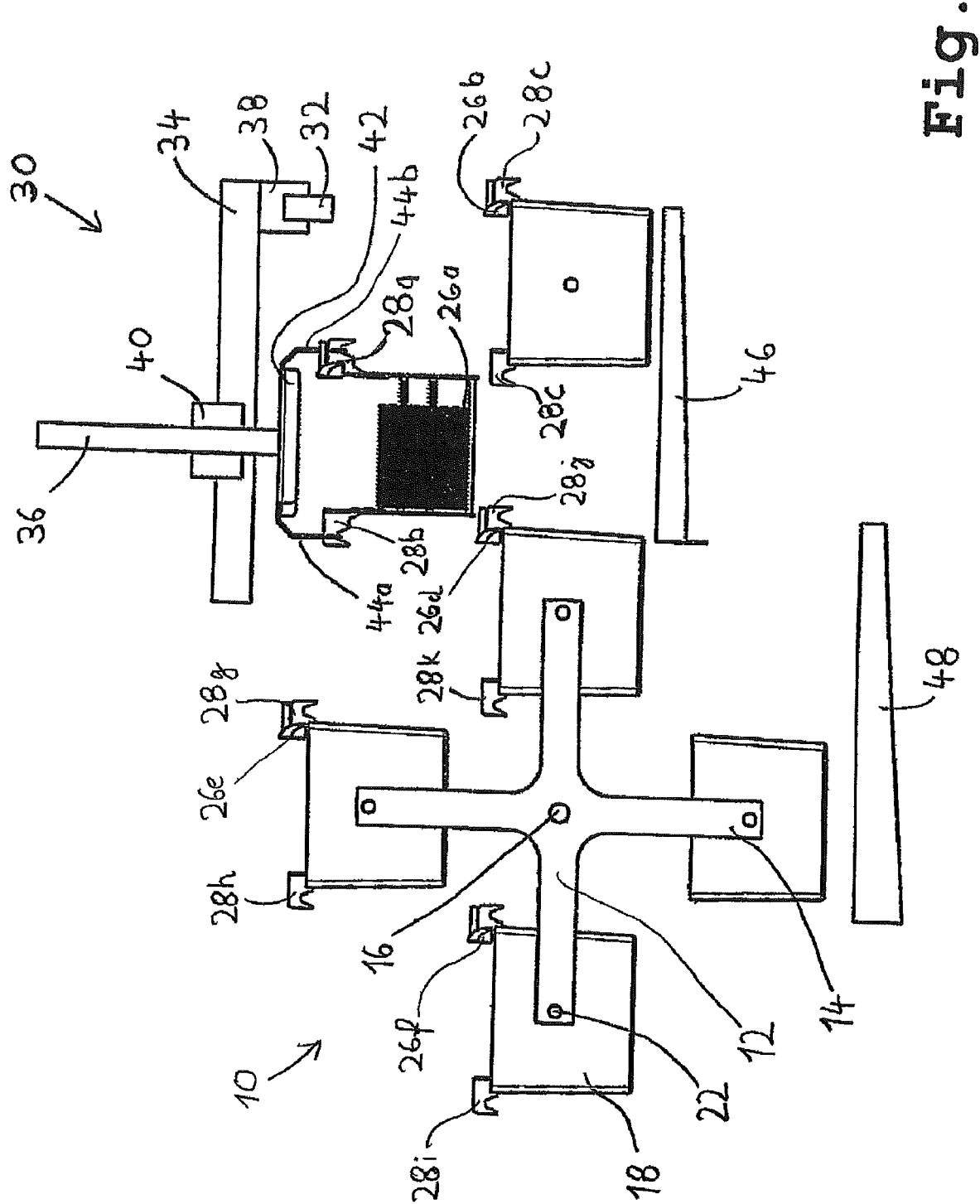
FIG. 2 is a frontal view of the apparatus for treating prepared specimens, in a working position.

FIG. 2 is a frontal view of the apparatus for treating prepared specimens, in the working position. Elements having the same configuration or the same function have the same reference characters.

Figure 3:
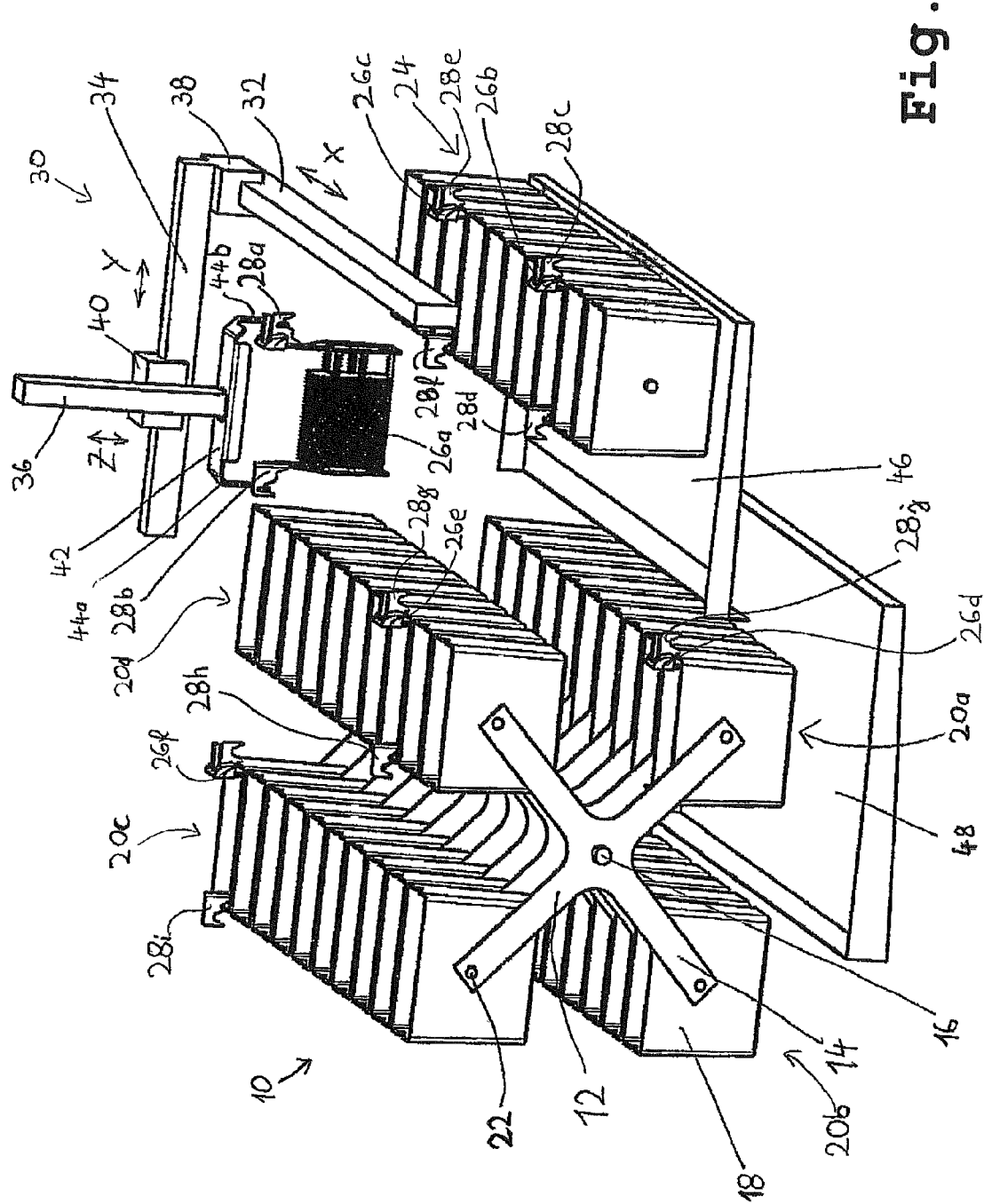
FIG. 3 is a further perspective depiction of the apparatus for treating prepared specimens.

FIG. 3 is a further perspective depiction of the apparatus for treating prepared specimens. Rotation unit 10 is not in the working position. FIG. 3 shows rotation unit 10 in a "snapshot" while rotation unit 10 is performing a rotary motion so that the container row 20a to 20d which contains reagent container 18 into which transport basket 26a to 26f is to be placed is aligned in such a way that said container row 20a to 20d faces toward stationary container row 24.

In an alternative embodiment of the invention, each holding element 12 can comprise more or fewer than four holding arms, 14, for example three or five holding arms 14. In addition, the distances between two adjacent holding elements 12 of rotation unit 10 can be different.

In a further alternative embodiment of the invention, transport mechanism 30 can comprise one linear axis and one or two pivotable arms.

LIST OF REFERENCE NUMERALS

10 Rotation unit
12 Holding element
14 Holding arm
16 Rotation shaft
18 Reagent container
20a to 20d Container row
22 Axle element
24 Stationary container row
26a to 26f Transport basket
28a to 28k Hook
30 Transport mechanism
32, 34, 36 Linear axis
38, 40 Slider
42 Gripper
44a, 44b Hook
46 Small drip pan
48 Large drip pan

The invention claimed is:

1. An apparatus for treating prepared specimens, comprising:
   at least two container rows arranged in parallel to each other, each comprising a plurality of reagent containers;
   a transport mechanism for transporting at least one transport container that receives at least one carrier holding at least one prepared specimen, the transport mechanism being movable at least in a first direction along an X axis extending along a longitudinal axis of the reagent containers, and in a second direction along a Z axis extending transversely to the X axis;
   a rotation unit comprising:
      holding arms; and
      at least one holding element; wherein
   the container rows are received rotatably at the ends of the holding arms of the at least one holding element that is connected to a rotation shaft such that it co-rotates with the rotation shaft that extends parallel to the X axis; and wherein
      the rotation unit is adapted to assume at least one working position allowing the transport mechanism to have access to the reagent container.

2. The apparatus according to claim 1, wherein the rotation unit comprises multiple cross-shaped holding elements that are connected to the rotation shaft such that they co-rotate with the rotation shaft that extends through a center of the holding elements.

3. The apparatus according to claim 1, wherein the transport mechanism comprises a further axis that extends orthogonally to the X axis and orthogonally to the Z axis.

4. The apparatus according to claim 1, wherein the transport mechanism comprises at least one gripper.

5. The apparatus according to claim 1, wherein the transport containers are transport baskets.

6. The apparatus according to claim 1, wherein the carriers are glass slides.

7. The apparatus according to claim 1, wherein the prepared specimens are biological thin sections.

8. The apparatus according to claim 1, wherein the apparatus comprises at least one stationary container row that is arranged outside the rotation unit and comprises a plurality of reagent containers.

9. The apparatus according to claim 1, wherein one reagent container each is rotatably mounted between each two adjacent holding elements of the rotation unit at the ends of the holding arms of the holding elements.

10. The apparatus according to claim 1, wherein the apparatus is adapted to stain the prepared specimens.

11. The apparatus according to claim 8, wherein a small drip pan is arranged underneath the stationary container row.

12. The apparatus according to claim 11, wherein a second drip pan is arranged underneath the rotation unit and the small drip pan.

13. The apparatus according to claim 1, wherein at least one holding arm of each holding element extends horizontally in the working position and the reagent container of the rotation unit that is being accessed by the transport mechanism is arranged on at least one of the horizontally extending holding arms in that container row facing the stationary container row.

* * * * *